(12) United States Patent
Wald et al.

(10) Patent No.: US 11,883,063 B2
(45) Date of Patent: Jan. 30, 2024

(54) MEDICAL DEVICE AND ITS CONSTRUCTION

(71) Applicant: Medtronic Xomed, Inc., Jacksonville, FL (US)

(72) Inventors: Andrew Wald, Denver, CO (US); Brad Jacobsen, Erie, CO (US); Charles R. Considine, Santa Rosa, CA (US); Frank Strupeck, Louisville, CO (US)

(73) Assignee: Medtronic Xomed, Inc., Jacksonville, FL (US)

( * ) Notice: Subject to any disclaimer, the term of this patent is extended or adjusted under 35 U.S.C. 154(b) by 1030 days.

(21) Appl. No.: 16/404,063

(22) Filed: May 6, 2019

(65) Prior Publication Data

US 2019/0254701 A1 Aug. 22, 2019

Related U.S. Application Data

(62) Division of application No. 13/871,616, filed on Apr. 26, 2013, now Pat. No. 10,278,729.

(51) Int. Cl.
| | |
|---|---|
| *A61B 17/34* | (2006.01) |
| *A61M 1/00* | (2006.01) |
| *A61B 17/24* | (2006.01) |
| *A61B 17/00* | (2006.01) |
| *A61B 90/40* | (2016.01) |
| *A61B 34/20* | (2016.01) |

(52) U.S. Cl.
CPC ....... *A61B 17/3421* (2013.01); *A61M 1/7411* (2021.05); *A61B 17/24* (2013.01); *A61B 90/40* (2016.02); *A61B 2017/00946* (2013.01); *A61B 2017/00964* (2013.01); *A61B 2034/2051* (2016.02); *Y10T 29/49826* (2015.01)

(58) Field of Classification Search
CPC .......... A61M 25/0009; A61M 25/0014; A61M 25/104; A61M 25/0152; A61M 2025/0034; A61M 2025/0039; A61M 1/76; A61B 17/3421; A61B 2017/3433; A61B 2017/00946; A61B 2017/00964
See application file for complete search history.

(56) References Cited

U.S. PATENT DOCUMENTS

| | | | |
|---|---|---|---|
| 2,312,993 | A | 3/1943 | Stephens |
| 3,568,660 | A | 3/1971 | Crites et al. |

(Continued)

FOREIGN PATENT DOCUMENTS

| | | |
|---|---|---|
| AU | 2011245296 A1 | 12/2012 |
| CA | 2797359 A1 | 11/2011 |

(Continued)

OTHER PUBLICATIONS

International Preliminary Report on Patentability dated Aug. 8, 2013 for PCT/US2012/022676 claiming benefit of U.S. Appl. No. 13/016,740, filed Jan. 28, 2011.

(Continued)

*Primary Examiner* — Jason E Flick
*Assistant Examiner* — Justin L Zamory
(74) *Attorney, Agent, or Firm* — Harness, Dickey & Pierce, P.L.C.

(57) ABSTRACT

A tube can include an elongated cannulated member that has an external wall. The tube can be navigated during a selected procedure. The tube can be shaped to selected configurations.

19 Claims, 5 Drawing Sheets

(56) References Cited

U.S. PATENT DOCUMENTS

| | | | |
|---|---|---|---|
| 4,188,979 A * | 2/1980 | Nakamura | B29C 63/42 |
| | | | 156/289 |
| 4,317,078 A | 2/1982 | Weed et al. | |
| 4,788,987 A | 12/1988 | Nickel | |
| 4,806,182 A | 2/1989 | Rydell et al. | |
| 4,813,210 A | 3/1989 | Masuda et al. | |
| 5,005,592 A | 4/1991 | Cartmell | |
| 5,057,120 A * | 10/1991 | Farcot | A61M 60/569 |
| | | | 604/99.01 |
| 5,226,423 A | 7/1993 | Tenerz et al. | |
| 5,234,416 A | 8/1993 | Macaulay et al. | |
| 5,391,199 A | 2/1995 | Ben-Haim | |
| 5,443,489 A | 8/1995 | Ben-Haim | |
| 5,538,511 A | 7/1996 | Van Antwerp | |
| 5,591,141 A | 1/1997 | Nettekoven | |
| 5,592,939 A | 1/1997 | Martinelli | |
| 5,645,559 A | 7/1997 | Hachtman et al. | |
| 5,693,085 A | 12/1997 | Buirge et al. | |
| 5,740,808 A | 4/1998 | Panescu et al. | |
| 5,749,357 A * | 5/1998 | Linder | A61M 16/0488 |
| | | | 128/207.14 |
| 5,762,637 A | 6/1998 | Berg et al. | |
| 5,840,024 A | 11/1998 | Taniguchi et al. | |
| 5,913,820 A | 6/1999 | Bladen et al. | |
| 5,938,602 A | 8/1999 | Lloyd | |
| 5,963,120 A | 10/1999 | Zaviska | |
| 5,983,126 A | 11/1999 | Wittkampf | |
| 6,010,529 A | 1/2000 | Herweck et al. | |
| 6,021,343 A | 2/2000 | Foley et al. | |
| 6,022,336 A * | 2/2000 | Zadno-Azizi | A61M 25/10184 |
| | | | 604/27 |
| 6,073,043 A | 6/2000 | Schneider | |
| 6,102,885 A | 8/2000 | Bass | |
| 6,106,486 A | 8/2000 | Tenerz et al. | |
| 6,201,387 B1 | 3/2001 | Govari | |
| 6,235,038 B1 | 5/2001 | Hunter et al. | |
| 6,253,770 B1 | 7/2001 | Acker et al. | |
| 6,254,600 B1 | 7/2001 | Willink et al. | |
| 6,332,891 B1 | 12/2001 | Himes | |
| 6,336,906 B1 | 1/2002 | Hammarstrom et al. | |
| 6,348,058 B1 | 2/2002 | Melkent et al. | |
| 6,381,485 B1 | 4/2002 | Hunter et al. | |
| 6,427,079 B1 | 7/2002 | Schneider et al. | |
| 6,434,507 B1 | 8/2002 | Clayton et al. | |
| 6,440,120 B1 * | 8/2002 | Maahs | A61F 2/013 |
| | | | 604/509 |
| 6,474,341 B1 | 11/2002 | Hunter et al. | |
| 6,478,802 B2 | 11/2002 | Kienzle, III et al. | |
| 6,556,857 B1 | 4/2003 | Estes et al. | |
| 6,610,066 B2 | 8/2003 | Dinger et al. | |
| 6,615,155 B2 | 9/2003 | Gilboa | |
| 6,616,651 B1 | 9/2003 | Stevens | |
| 6,687,531 B1 | 2/2004 | Ferre et al. | |
| 6,689,049 B1 | 2/2004 | Miyagi et al. | |
| 6,695,764 B2 | 2/2004 | Silverman et al. | |
| 6,747,539 B1 | 6/2004 | Martinelli | |
| 6,796,988 B2 | 9/2004 | Melkent et al. | |
| 6,833,814 B2 | 12/2004 | Gilboa et al. | |
| 6,926,674 B2 | 8/2005 | Tenerz et al. | |
| 6,940,941 B2 | 9/2005 | Gregerson et al. | |
| 6,977,575 B2 | 12/2005 | Bernier | |
| 6,980,849 B2 | 12/2005 | Sasso | |
| 6,993,374 B2 | 1/2006 | Sasso | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,118,378 B1 | 10/2006 | Karapetyan | |
| 7,135,978 B2 | 11/2006 | Gisselberg et al. | |
| 7,153,308 B2 | 12/2006 | Peterson | |
| 7,166,114 B2 | 1/2007 | Moctezuma De La Barrera et al. | |
| 7,188,998 B2 | 3/2007 | Gregerson et al. | |
| 7,226,456 B2 | 6/2007 | O'Neil et al. | |
| 7,289,839 B2 | 10/2007 | Dimmer et al. | |
| 7,346,417 B2 | 3/2008 | Luth et al. | |
| 7,366,562 B2 | 4/2008 | Dukesherer et al. | |
| 7,410,480 B2 | 8/2008 | Muni et al. | |
| 7,462,175 B2 | 12/2008 | Chang et al. | |
| 7,500,971 B2 | 3/2009 | Chang et al. | |
| 7,537,594 B2 | 5/2009 | Sartor | |
| 7,559,137 B2 | 7/2009 | Beer et al. | |
| 7,604,609 B2 | 10/2009 | Jervis | |
| 7,625,617 B1 | 12/2009 | Anderson et al. | |
| 7,629,015 B2 | 12/2009 | Anderson et al. | |
| 7,637,896 B2 | 12/2009 | Voegele et al. | |
| 7,647,083 B2 | 1/2010 | Al-Ali et al. | |
| 7,657,301 B2 | 2/2010 | Mate et al. | |
| 7,697,972 B2 | 4/2010 | Verard et al. | |
| 7,751,865 B2 | 7/2010 | Jascob et al. | |
| 7,763,035 B2 | 7/2010 | Melkent et al. | |
| 7,774,933 B2 | 8/2010 | Wilson et al. | |
| 7,797,032 B2 | 9/2010 | Martinelli et al. | |
| 7,818,044 B2 | 10/2010 | Dukesherer et al. | |
| 7,840,253 B2 | 11/2010 | Tremblay et al. | |
| 7,844,319 B2 | 11/2010 | Susil et al. | |
| 7,881,769 B2 | 2/2011 | Sobe | |
| 7,971,341 B2 | 7/2011 | Dukesherer et al. | |
| 7,979,032 B2 | 7/2011 | Lomnitz | |
| 8,075,969 B2 | 12/2011 | Anderson et al. | |
| 8,086,298 B2 | 12/2011 | Whitmore, III et al. | |
| 8,105,339 B2 | 1/2012 | Melkent et al. | |
| 8,147,486 B2 | 4/2012 | Honour et al. | |
| 8,239,001 B2 | 8/2012 | Verard et al. | |
| 8,251,949 B2 | 8/2012 | Warnack | |
| 8,255,027 B2 | 8/2012 | Al-Ali et al. | |
| 8,320,991 B2 | 11/2012 | Jascob et al. | |
| 8,504,139 B2 | 8/2013 | Jacobsen et al. | |
| 8,644,907 B2 | 2/2014 | Hartmann et al. | |
| 8,648,605 B2 | 2/2014 | Nakamura et al. | |
| 8,674,694 B2 | 3/2014 | Hyde et al. | |
| 8,862,204 B2 | 10/2014 | Sobe et al. | |
| 9,226,688 B2 | 1/2016 | Jacobsen et al. | |
| 9,226,689 B2 | 1/2016 | Jacobsen et al. | |
| 9,226,800 B2 | 1/2016 | Burg et al. | |
| 9,232,985 B2 | 1/2016 | Jacobsen et al. | |
| 9,480,415 B2 | 11/2016 | Wald et al. | |
| 9,504,530 B2 | 11/2016 | Hartmann et al. | |
| 9,623,208 B2 | 4/2017 | Wright et al. | |
| 9,750,486 B2 | 9/2017 | Burg et al. | |
| 9,974,501 B2 | 5/2018 | Hartmann et al. | |
| 10,278,729 B2 | 5/2019 | Wald et al. | |
| 10,492,868 B2 | 12/2019 | Hartmann et al. | |
| 10,568,699 B2 | 2/2020 | Jacobsen et al. | |
| 2001/0034549 A1 | 10/2001 | Bartholf et al. | |
| 2002/0133141 A1 | 9/2002 | Sparks et al. | |
| 2002/0153015 A1 | 10/2002 | Garibaldi et al. | |
| 2002/0165448 A1 | 11/2002 | Ben-Haim et al. | |
| 2002/0167313 A1 | 11/2002 | Taimisto | |
| 2003/0009095 A1 | 1/2003 | Skarda | |
| 2003/0050552 A1 | 3/2003 | Vu | |
| 2003/0187347 A1 | 10/2003 | Nevo et al. | |
| 2003/0216639 A1 | 11/2003 | Gilboa et al. | |
| 2003/0236549 A1 | 12/2003 | Bonadio et al. | |
| 2004/0097804 A1 | 5/2004 | Sobe | |
| 2004/0116803 A1 | 6/2004 | Jascob et al. | |
| 2004/0199072 A1 | 10/2004 | Sprouse et al. | |
| 2004/0215071 A1 | 10/2004 | Frank et al. | |
| 2005/0027339 A1 | 2/2005 | Schrom et al. | |
| 2005/0027340 A1 | 2/2005 | Schrom et al. | |
| 2005/0027341 A1 | 2/2005 | Schrom et al. | |
| 2005/0059885 A1 | 3/2005 | Melkent et al. | |
| 2005/0060885 A1 | 3/2005 | Johnson et al. | |
| 2005/0085715 A1 | 4/2005 | Dukesherer et al. | |
| 2005/0085720 A1 | 4/2005 | Jascob et al. | |
| 2005/0105212 A1 | 5/2005 | Sato | |
| 2005/0137576 A1 | 6/2005 | Packard | |
| 2005/0154294 A1 | 7/2005 | Uchiyama et al. | |
| 2005/0171508 A1 | 8/2005 | Gilboa | |
| 2005/0215922 A1 | 9/2005 | Tsonton et al. | |
| 2005/0222554 A1 | 10/2005 | Wallace et al. | |
| 2006/0004286 A1 | 1/2006 | Chang et al. | |
| 2006/0025677 A1 | 2/2006 | Verard et al. | |
| 2006/0036189 A1 | 2/2006 | Martinelli et al. | |
| 2006/0084867 A1 | 4/2006 | Tremblay et al. | |

(56) References Cited

U.S. PATENT DOCUMENTS

| | | |
|---|---|---|
| 2006/0095066 A1 | 5/2006 | Chang et al. |
| 2006/0129061 A1 | 6/2006 | Kaneto et al. |
| 2006/0142656 A1 | 6/2006 | Malackowski et al. |
| 2006/0173284 A1 | 8/2006 | Ackerman et al. |
| 2006/0206039 A1 | 9/2006 | Wilson et al. |
| 2006/0206170 A1 | 9/2006 | Denker et al. |
| 2006/0212056 A1* | 9/2006 | Salvadori ............ A61M 1/7411 606/167 |
| 2006/0224142 A1 | 10/2006 | Wilson et al. |
| 2006/0229624 A1 | 10/2006 | May et al. |
| 2006/0235314 A1 | 10/2006 | Migliuolo et al. |
| 2006/0271097 A1 | 11/2006 | Ramzipoor et al. |
| 2007/0032862 A1 | 2/2007 | Weber et al. |
| 2007/0088416 A1 | 4/2007 | Atalar et al. |
| 2007/0157828 A1 | 7/2007 | Susel et al. |
| 2007/0167930 A1 | 7/2007 | Eversull et al. |
| 2007/0197899 A1 | 8/2007 | Ritter et al. |
| 2007/0208252 A1 | 9/2007 | Makower |
| 2007/0220746 A1 | 9/2007 | Anderson et al. |
| 2007/0225595 A1 | 9/2007 | Malackowski et al. |
| 2007/0255132 A1 | 11/2007 | Shalgi et al. |
| 2008/0058767 A1 | 3/2008 | Rotman et al. |
| 2008/0097195 A1 | 4/2008 | Urquhart et al. |
| 2008/0097347 A1 | 4/2008 | Arvanaghi |
| 2008/0119727 A1 | 5/2008 | Barbagli et al. |
| 2008/0119919 A1 | 5/2008 | Atalar et al. |
| 2008/0132909 A1 | 6/2008 | Jascob et al. |
| 2008/0154296 A1 | 6/2008 | Taylor et al. |
| 2008/0171934 A1 | 7/2008 | Greenan et al. |
| 2008/0171937 A1 | 7/2008 | Dukesherer et al. |
| 2008/0172069 A1 | 7/2008 | Dukesherer et al. |
| 2008/0228195 A1 | 9/2008 | von Jako et al. |
| 2009/0088728 A1 | 4/2009 | Dollar et al. |
| 2009/0118742 A1 | 5/2009 | Hartmann et al. |
| 2009/0171187 A1 | 7/2009 | Gerhart et al. |
| 2009/0204023 A1 | 8/2009 | Goldenberg |
| 2009/0209947 A1 | 8/2009 | Gordin et al. |
| 2010/0063383 A1 | 3/2010 | Anderson et al. |
| 2010/0081965 A1 | 4/2010 | Mugan et al. |
| 2010/0087789 A1 | 4/2010 | Leeflang et al. |
| 2010/0130852 A1 | 5/2010 | Neidert et al. |
| 2010/0134096 A1 | 6/2010 | Chiba et al. |
| 2010/0145337 A1 | 6/2010 | Janna et al. |
| 2010/0185083 A1 | 7/2010 | Neidert et al. |
| 2010/0210939 A1 | 8/2010 | Hartmann et al. |
| 2010/0228117 A1 | 9/2010 | Hartmann |
| 2010/0234724 A1 | 9/2010 | Jacobsen et al. |
| 2010/0253361 A1 | 10/2010 | Nakamura et al. |
| 2010/0280363 A1 | 11/2010 | Skarda et al. |
| 2010/0331763 A1 | 12/2010 | Wilson et al. |
| 2011/0014705 A1 | 1/2011 | Leach et al. |
| 2011/0060214 A1 | 3/2011 | Makower |
| 2011/0060276 A1 | 3/2011 | Schaeffer et al. |
| 2011/0066029 A1 | 3/2011 | Lyu et al. |
| 2011/0118592 A1 | 5/2011 | Sobe et al. |
| 2011/0251519 A1 | 10/2011 | Romoscanu |
| 2011/0258842 A1 | 10/2011 | Dukesherer et al. |
| 2011/0270081 A1* | 11/2011 | Burg ................... A61B 34/20 600/424 |
| 2012/0112746 A1 | 5/2012 | Hyde et al. |
| 2012/0172696 A1 | 7/2012 | Kallback et al. |
| 2012/0197108 A1 | 8/2012 | Hartmann et al. |
| 2012/0197109 A1 | 8/2012 | Hartmann et al. |
| 2012/0197110 A1 | 8/2012 | Hartmann et al. |
| 2012/0245665 A1 | 9/2012 | Friedman et al. |
| 2012/0271135 A1 | 10/2012 | Burke et al. |
| 2012/0283570 A1 | 11/2012 | Tegg |
| 2013/0066194 A1 | 3/2013 | Seter et al. |
| 2013/0137954 A1 | 5/2013 | Jacobsen et al. |
| 2013/0317355 A1 | 11/2013 | Jacobsen et al. |
| 2014/0012130 A1 | 1/2014 | Jacobsen et al. |
| 2014/0021213 A1 | 1/2014 | Caplan |
| 2014/0276004 A1 | 1/2014 | Strupeck et al. |
| 2014/0148692 A1 | 5/2014 | Hartmann et al. |
| 2014/0158555 A1 | 6/2014 | Nakamura et al. |
| 2015/0005625 A1 | 1/2015 | Sobe et al. |
| 2018/0055580 A1 | 3/2018 | Burg et al. |

FOREIGN PATENT DOCUMENTS

| | | |
|---|---|---|
| CN | 101621966 A | 1/2010 |
| CN | 103068332 A | 4/2013 |
| DE | 102009030731 A1 | 12/2010 |
| EP | 0425319 A2 | 5/1991 |
| EP | 1302172 A1 | 4/2003 |
| EP | 1510182 A2 | 3/2005 |
| EP | 1552795 A1 | 7/2005 |
| EP | 1658818 A1 | 5/2006 |
| EP | 1743591 A2 | 1/2007 |
| EP | 1806756 A2 | 7/2007 |
| EP | 2114263 A2 | 11/2009 |
| EP | 2123220 A1 | 11/2009 |
| EP | 2563260 A2 | 3/2013 |
| JP | 2000151041 A | 5/2000 |
| JP | 03-207344 B2 | 9/2001 |
| JP | 2006167119 A | 6/2006 |
| JP | 2007-527296 A | 9/2007 |
| JP | 2008-155033 A | 7/2008 |
| JP | 2008194475 A | 8/2008 |
| JP | 2010082446 A | 4/2010 |
| WO | 9632060 A1 | 10/1996 |
| WO | 9729682 A1 | 8/1997 |
| WO | 9729684 A1 | 8/1997 |
| WO | 9940856 A1 | 8/1999 |
| WO | 0038571 A1 | 7/2000 |
| WO | 0134050 A2 | 5/2001 |
| WO | 2006116597 A2 | 1/2006 |
| WO | 2006096685 A1 | 9/2006 |
| WO | 2007/061890 A2 | 5/2007 |
| WO | 2008054423 A1 | 5/2008 |
| WO | 2008105874 A1 | 9/2008 |
| WO | 2009152486 A1 | 12/2009 |
| WO | 2010049834 A1 | 5/2010 |
| WO | 2010142285 A1 | 10/2010 |
| WO | 2010144419 A2 | 12/2010 |
| WO | 2011137301 A2 | 11/2011 |
| WO | 2012103304 | 8/2012 |
| WO | 2012103304 A1 | 8/2012 |
| WO | 2012103407 A1 | 8/2012 |
| WO | 2012103410 A1 | 8/2012 |
| WO | 2013062869 A1 | 5/2013 |
| WO | 2014116961 A1 | 7/2014 |
| WO | 2014176065 A1 | 10/2014 |

OTHER PUBLICATIONS

International Preliminary Report on Patentability dated Aug. 8, 2013 for PCT/US2012/022840 claiming benefit of U.S. Appl. No. 13/016,762, filed Jan. 28, 2011.

International Preliminary Report on Patentability dated Aug. 8, 2013 for PCT/US2012/022846 claiming benefit of U.S. Appl. No. 13/016,765, filed Jan. 28, 2011.

International Preliminary Report on Patentability dated Nov. 15, 2012 for PCT/US2011/34475 claiming benefit of U.S. Appl. No. 13/097,243, filed Apr. 29, 2011.

International Preliminary Report on Patentability dated Oct. 27, 2015 for PCT/US2014/034022 claiming benefit of U.S. Appl. No. 13/871,616, filed Apr. 26, 2013.

International Search Report and Written Opinion dated Oct. 27, 2014 for PCT/US2014/028100 claiming benefit of U.S. Appl. No. 14/209,696, filed Mar. 13, 2014.

International Search Report and Written Opinion dated Apr. 23, 2014 for PCT/US2014/012786 claiming benefit of U.S. Appl. No. 13/748,150, filed Jan. 23, 2013.

International Search Report and Written Opinion dated Feb. 6, 2013 for PCT/US2012/061086 claiming benefit of U.S. Appl. No. 13/281,001, filed Oct. 25, 2011.

International Search Report and Written Opinion dated Jul. 6, 2012 for PCT/US2012/022840 claiming benefit to U.S. Appl. No. 13/016,762, filed Jan. 28, 2011.

(56) References Cited

OTHER PUBLICATIONS

International Search Report and Written Opinion dated May 12, 2014 for PCT/US2014/012967 claiming benefit of U.S. Appl. No. 13/751,032, filed Jan. 25, 2013.
International Search Report and Written Opinion dated May 9, 2012 for PCT/US2012/022676 claiming benefit of U.S. Appl. No. 13/016,740, filed Jan. 28, 2011.
International Search Report and Written Opinion dated May 9, 2012 for PCT/US2012/022846 claiming benefit of U.S. Appl. No. 13/016,765, filed Jan. 28, 2011.
International Search Report and Written Opinion dated Oct. 31, 2011, claiming benefit of U.S. Appl. No. 13/097,243, filed Apr. 29, 2011.
International Search Report dated Jul. 15, 2010 for PCT/US2010/026655 claiming benefit of U.S. Appl. No. 12/400,451, filed Mar. 10, 2009.
International Search Report dated Jul. 31, 2014 for PCT/US2014/034022 claiming benefit of U.S. Appl. No. 13/871,616, filed Apr. 26, 2013.
Invitation to Pay Additional Fees and Where Applicable, Protest Fee dated Aug. 14, 2014 for PCT/US2014/028100 claiming benefit of U.S. Appl. No. 14/209,696, filed Mar. 13, 2014.
Invitation to Pay Additional Fees dated Dec. 17, 2012 for PCT/US2012/061086 claiming benefit of U.S. Appl. No. 13/281,001, filed Oct. 25, 2011.
Invitation to Pay Additional Fees dated Jul. 25, 2011, claiming benefit of U.S. Appl. No. 13/097,243, filed Apr. 29, 2011.
Invitation to Pay Additional Fees dated May 8, 2012 for PCT/US2012/022840 claiming benefit of U.S. Appl. No. 13/016,762, filed Jan. 28, 2011.
Japanese Office Action dated Aug. 29, 2016 for JP Application No. 2015-555345 corresponding to PCT/US2014/012967 which claims benefit of U.S. Appl. No. 13/751,032, filed Jan. 25, 2013.
Japanese Office Action dated Jan. 7, 2014 for Japan Application No. 2013-508273 claiming benefit of U.S. Appl. No. 13/097,243, filed Apr. 29, 2011.
Japanese Office Action dated Sep. 13, 2016 for JP Application No. 2016-510697 corresponding to PCT/US2014/034022 which claims benefit of U.S. Appl. No. 13/871,616, filed Apr. 26, 2013.
Japanese Office Action dated Sep. 13, 2016 for JP Application No. 2016-510697 corresponding to PCT/US2014/034022 which claimss benefit of U.S. Appl. No. 13/871,616, filed Apr. 26, 2013.
Japanese Office Action dated Dec. 1, 2017 in corresponding/related Japanese Application No. 2016-510697.
Japanese Office Action dated Jul. 3, 2017 in corresponding Japanese Application No. 2015-555278.
Japanese Office Action dated May 19, 2017 for Japanese Application No. 2016-510697 corresponding to PCT/US2014/034022 which claims benefit of U.S. Appl. No. 13/871,616, filed Apr. 26, 2013.
Medtronic Navigation, "StealthStationâ AXIEM™ Electromagnetic Navigation . . . ", 2005, www.stealthstation.com/physician/spine/library/axiem_ent.jsp, printed Aug. 19, 2006 (2 pages).
Office Action regarding Canadian Patent Application No. 2,898,485, dated Feb. 13, 2020.
Office Action dated Sep. 14, 2020, in corresponding/related European Application No. 14721108.0.
Office Action dated Nov. 25, 2020, in corresponding/related Canadian Application No. 3,056,567.
Office Action dated Jul. 10, 2020 in corresponding/related Korean Application No. 10-2015-7021532.
Office Action dated Sep. 21, 2020 in corresponding/related Korean Application No. 10-2015-7032034.
"Flexible electronics," Dec. 19, 2012 (Dec. 19, 2012), XP055112518, en.wikipedia.org. Retrieved form the Internet: <URL:http://en.wikipedia.org/w/index.php?title=Flexible_electronics&oldid=528841651> [retrieved on Apr. 7, 2014]. (6 sheets).
"Flexible Printed Circuit Manufacturer—Capabilities," Aug. 16, 2012 (Aug. 16, 2012), XP055112534, fpcexpress.com. Retrieved from the Internet: URL: <http://web.archive.org/web/20120816030431/http://fpcexpress.com/capabilities.html1>. [retrieved on Apr. 7, 2014][retrieved on May 8, 2014]. (3 sheets).
"InstaTrak 3500 Plus. Applications: ENT. Cranial." http://www.gehealthcare/usen/xr/surgery/products/nav.html (printed Dec. 14, 2009).
"InstaTrak™ 3500 plus—Cranial. Multi-application electromagnetic surgical navigation system for ENT, Cranial, and Spine procedures." GE Healthcare http://www.gehealthcare.com/euen/surgery/products/instatrak-3500-plus-cranial/index.html (printed Dec. 14, 2009).
"InstaTrak™ 3500 plus—ENT. Multi-application electromagnetic surgical navigation system for ENT and Cranial." GE Healthcare http://www.gehealthcare.com/euen/surgery/products/instatrak-3500-plus-ent/index.html (printed Dec. 14, 2009).
"Insta Trak® Image Guided Sinus Surgery, Introduction to the InstaTrak System." Sinus-Clear.com http:/www.sinus-clear.com/instatrak.htm (printed Dec. 14, 2009).
"Mayfield® Skull Clamps and Headrest Systems," Mayfield® Surgical Devices Product Index, pp. 1-6, Dec. 2004 Integra LifeSciences Corporation.
"Medtronic O-Arm Multi-Dimensional Surgical Imaging System"; Brochure, Minco, 24pp, 2009.
"Minco Bulletin FC-3," Jul. 31, 2002 (Jul. 31, 2002). XP055115671, Retrieved from the Internet: <URL:http://www.temflexcontrols.com/pdf/fc3.pdf> [retrieved on Apr. 29, 2014]. (1 sheet).
"Sectional design standard for flexible printed boards," Internet Citation, Nov. 30, 1998 (Nov. 30, 1998), pp. 1-35, XP002691487, Retrieved form the Interent: <URL:http://222.184.16.210/smt/tzxt/bz/IPC-2223.pdf>. [retrieved on Feb. 1, 2013].
"StealthStation_S7_System® Information Center in the OR," (2009) Medtronic, Inc.
"StealthStation® TRIA™ plus Treatment Guidance System," brochure, Medtronic Surgical Navigation Technologies (2004) 2 pages.
"The doctor can see you now" brochure. GE Medical Systems (2003) General Electric Company.
"TREON, StealthStation," brochure, Medtronic Surgical Navigation Technologies (2001) 8 pages.
Acclarent™ "Instructions for Use. Balloon Sinuplasty™ System. Relieva™ Devices, ReliENT™ Navigation System, and OptiLINK™ Extension." (Aug. 21, 2009) pp. 1-13.
Acclarent™ "Instructions for Use. Relieva FlexO Sinus Guide Catheter, Relieva® Sinus Guide Catheter." (Sep. 19, 2009) pp. 1-6.
Australian Office Action dated Apr. 10, 2018 in corresponding/related Australian Application No. 2014257385.
Australian Office Action dated Aug. 22, 2017 in corresponding Australian Application No. 2014209323.
Australian Office Action dated Sep. 21, 2018 in corresponding/related Australian Application No. 2014209251.
Australian Office Action dated Sep. 27, 2017 in corresponding/related Australian Application No. 2014209251.
Canadian Office Action dated Jul. 6, 2018 in corresponding/related Canadian Application No. 2,942,656.
Canadian Office Action dated Oct. 24, 2017 in corresponding/related Canadian Application No. 2,942,656.
Chinese Office Action dated Apr. 3, 2015 for Chinese Application No. 201180031075.0 claiming benefit of PCT/US2011/034475 filed Apr. 29, 2011, claiming benefit from U.S. Appl. No. 61/330,024, filed Apr. 30, 2010 and U.S. Appl. No. 13/097,243, filed Apr. 29, 2011.
Chinese Office Action dated Feb. 4, 2017 for Chinese Application No. 2014800059516.
Chinese Office Action dated Mar. 9, 2017 for Chinese Application No. 201480004264.2.
Chinese Office Action dated Sep. 3, 2014 for Chinese Application No. 201180031075.0 claiming benefit of PCT/US2011/034475 filed Apr. 29, 2011, claiming benefit from U.S. Appl. No. 61/330,024, filed Apr. 30, 2010 and U.S. Appl. No. 13/097,243, filed Apr. 29, 2011.
Chinese Office Action dated Aug. 29, 2017 in corresponding Chinese Application No. 201480005951.6.
Chinese Office Action dated Jun. 29, 2017 in corresponding Chinese Application No. 201480023678.X.

(56) References Cited

OTHER PUBLICATIONS

Chinese Office Action dated Mar. 23, 2018 in corresponding/related Chinese Application No. 201480023678.X.
Chinese Office Action dated Oct. 30, 2017 in corresponding/related Chinese Application No. 201610206046.8.
Chinese Office Action dated Sep. 25, 2017 in corresponding Chinese Application No. 201480004264.2.
Communication pursuant to Article 94(3) EPC dated Feb. 1, 2017 for European Application No. 11799331 corresponding to PCT/US2011/034475 filed Apr. 11, 2011.
Communication pursuant to Article 94(3) EPC dated Nov. 24, 2016 for European Application No. 107084790 corresponding to PCT/US2010-026655 claiming benefit of U.S. Appl. No. 12/400,951, filed Mar. 10, 2009.
Communication pursuant to Article 94(3) EPC for European Application No. 12703208.4-1654 dated Apr. 24, 2015.
European Office Action dated Mar. 1, 2017 for European Application No. 12709722.8.
European Office Action dated Apr. 13, 2017 in European Application No. 14721108.0 corresponding to PCT/US2014/028100 which claims priority to U.S. Appl. No. 14/209,696, filed Mar. 13, 2014 and U.S. Appl. No. 61/790,479, filed Mar. 15, 2013.
European Office Action dated Jun. 22, 2017 in corresponding European Application No. 14703512.5.
European Office Action dated Mar. 19, 2018 in corresponding/related European Application No. 17208055.8.
European Office Action dated May 3, 2018 in corresponding European Application No. 14725316.5.
European Office Action dated Nov. 23, 2017 in corresponding/related European Application No. 14721108.0.
European Office Action dated Nov. 9, 2017 in corresponding/related European Application No. 11719933.1.
Examiner's Report dated Dec. 18, 2013 for Canadian Application No. 2,797,359 claiming benefit of U.S. Appl. No. 13/097,243, filed Apr. 29, 2011.
http://oxforddictionaries.com/definition/english/barrel (accessed Dec. 3, 2012).
International Preliminary Report on Patentability and Written Opinion dated May 8, 2014 for PCT/US2012/061086 claiming benefit of U.S. Appl. No. 13/281,001, filed Oct. 25, 2011.
International Preliminary Report on Patentability and Written Opinion dated Aug. 6, 2015 for PCT/US2014/012786 claiming benefit of U.S. Appl. No. 13/748,150, filed Jan. 23, 2013.
International Preliminary Report on Patentability and Written Opinion dated Aug. 6, 2015 for PCT/US2014/012786 claiming benefit of U.S. Appl. No. 13/748,150, filed Jan. 23, 2012.
International Preliminary Report on Patentability and Written Opinion dated Aug. 6, 2015 for PCT/US2014/012967 claiming benefit of U.S. Appl. No. 13/751,032, filed Jan. 25, 2013.
International Preliminary Report on Patentability and Written Opinion dated Sep. 22, 2011 for PCT/US2010/026655 claiming benefit of U.S. Appl. No. 12/400,451, filed Mar. 10, 2009.
International Preliminary Report on Patentability and Written Opinion dated Sep. 24, 2015 for PCT/US2014/028100 claiming benefit to U.S. Appl. No. 14/209,696, filed Mar. 13, 2014.
Office Action dated Mar. 15, 2019 in corresponding/related European Application No. 17208055.8.
U.S. Appl. No. 13/016,765, U.S. Pat. No. 9,974,501, filed Jan. 28, 2011, Hartmann.
U.S. Appl. No. 13/281,001, U.S. Pat. No. 9,750,486, filed Oct. 25, 2011, Burg.
U.S. Appl. No. 12/400,951, U.S. Pat. No. 8,504,139, filed Mar. 10, 2009, Jacobsen.
U.S. Appl. No. 13/959,123, U.S. Pat. No. 9,232,985, filed Aug. 5, 2013, Jacobsen.
U.S. Appl. No. 13/097,243, U.S. Pat. No. 9,226,800, filed Apr. 29, 2011, Burg.
U.S. Appl. No. 13/748,150, U.S. Pat. No. 9,226,688, filed Jan. 23, 2013, Jacobsen.
U.S. Appl. No. 13/751,032, U.S. Pat. No. 9,226,689, filed Jan. 25, 2013, Jacobsen.
U.S. Appl. No. 13/871,616, U.S. Pat. No. 10,278,729, filed Apr. 26, 2019, Wald.
U.S. Appl. No. 13/016,740, 2012/0197108, filed Jan. 28, 2011, Hartmann.
U.S. Appl. No. 13/016,762, 2012/0197109, filed Jan. 28, 2011, Hartmann.
U.S. Appl. No. 14/209,696, 2014/0276004, filed Mar. 13, 2014, Strupeck.
U.S. Appl. No. 14/992,418, 2016/0120609, filed Jan. 11, 2016, Jacobsen.
U.S. Appl. No. 14/987,033, 2016/0113729, filed Jan. 4, 2016, Burg.
U.S. Appl. No. 15/804,600, 2018/0055580, filed Nov. 6, 2017, Hartmann.
U.S. Appl. No. 16/404,002, filed May 6, 2019, Wald.
Extended European Search Report dated Sep. 9, 2019 in corresponding/related European Application No. 19179149.0.
Extended European Search Report, dated Sep. 20, 2019, in corresponding/related European Application No. 19171550.7.
Australian Office Action dated Sep. 27, 2017 in corresponding Australian Application No. 2014209251.
Communication pursuant to Article 94(3) EPC for EP Patent Application No. 12703208.4 dated Jan. 27, 2016.
European Office Action corresponding to European Application No. 19179149.0-1122 dated Sep. 9, 2019.
European Office Action dated Oct. 20, 2015 for European Application No. 127841781 claiming benefit of PCT/US2012/061086 filed Oct. 19, 2012.
European Office Action dated Apr. 13, 2017 in corresponding European Application No. 14706985.0.
Office Action regarding Canadian Patent Application No. 2898636, dated Jan. 7, 2020.
European Office Action, corresponding to EP191715507, dated May 16, 2023.

\* cited by examiner

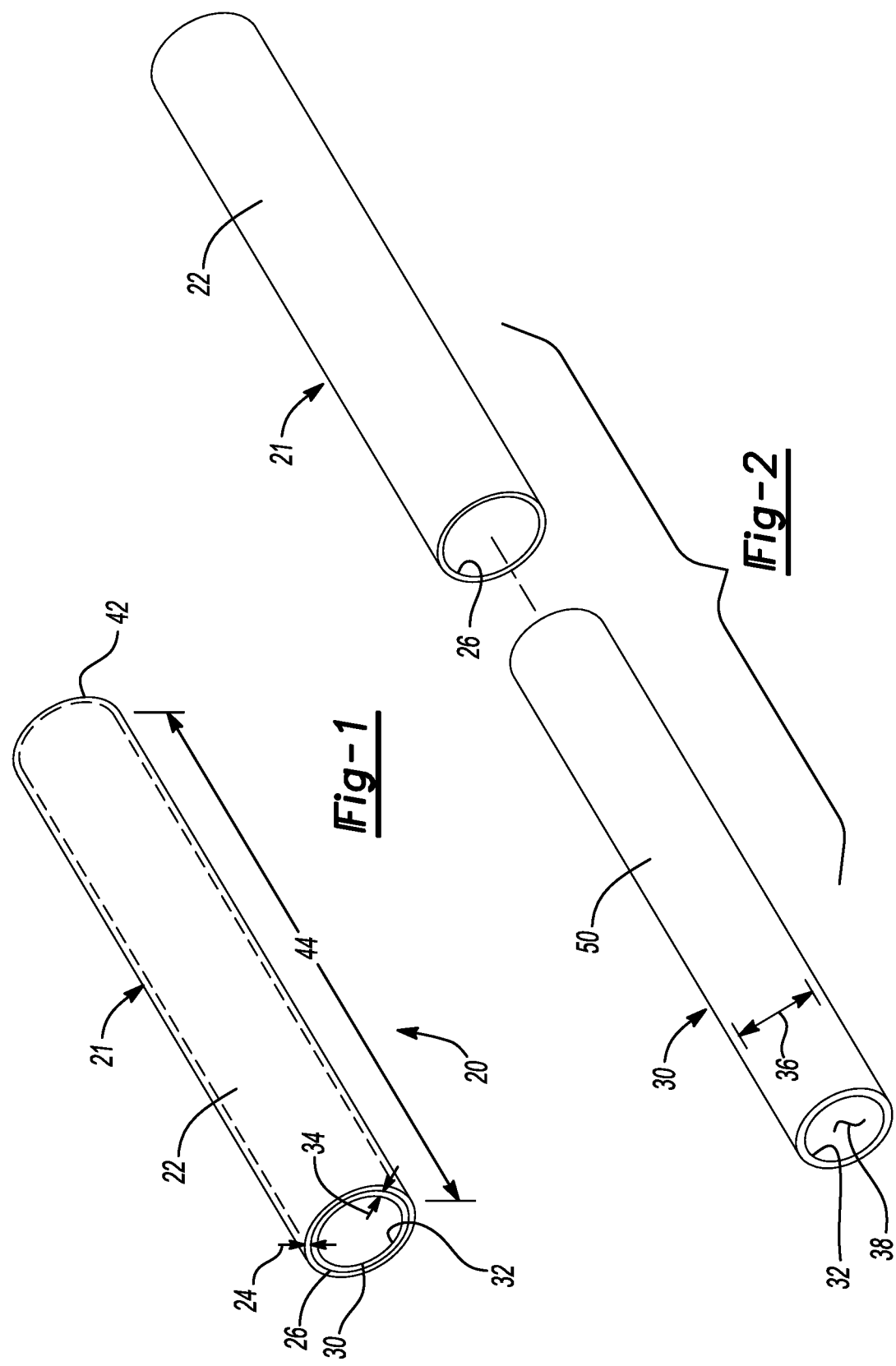

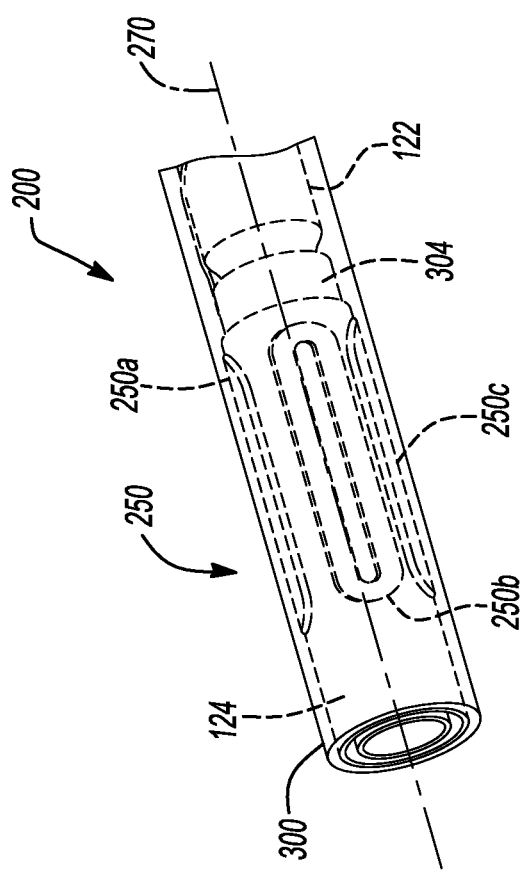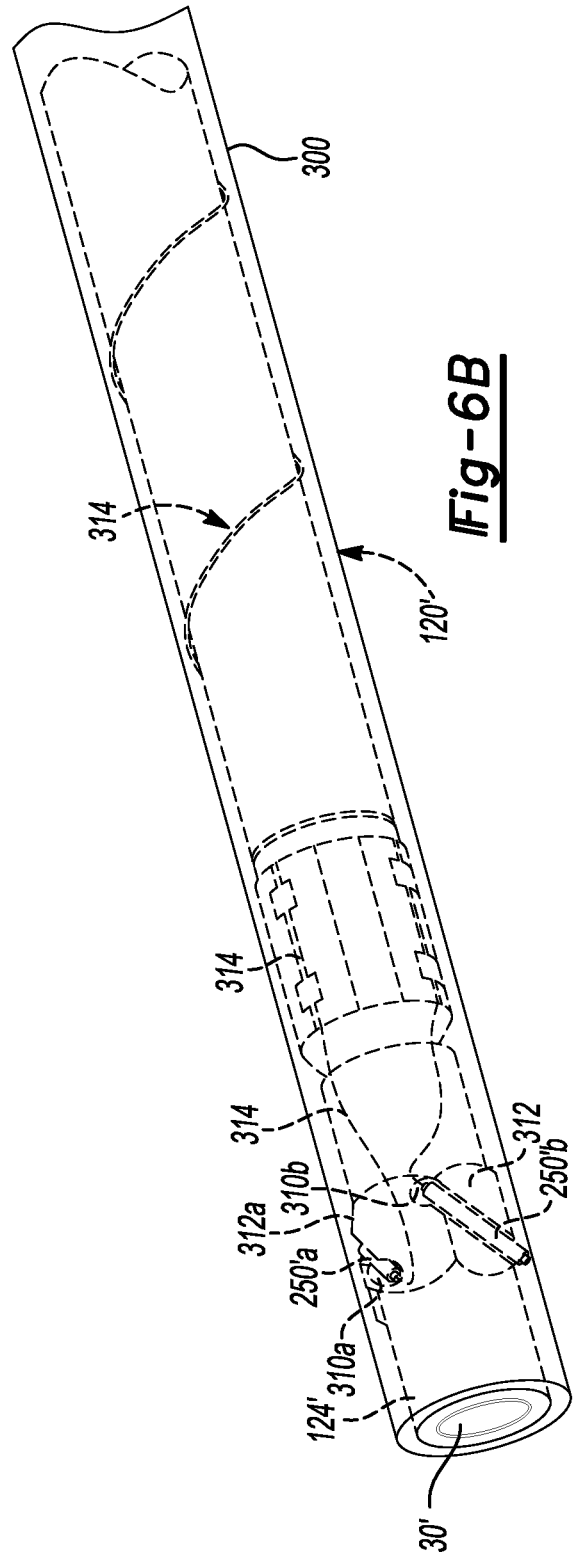

US 11,883,063 B2

MEDICAL DEVICE AND ITS CONSTRUCTION

The application is a divisional of U.S. patent application Ser. No. 13/871,616 filed on Apr. 26, 2013. The entire disclosure of the above application is incorporated herein by reference.

FIELD

The subject disclosure is related generally to a medical instrument, and particularly to a cannulated tube having an internal coating.

BACKGROUND

This section provides background information related to the present disclosure which is not necessarily prior art.

Instruments can be used to perform various procedures on a patient. For example, a probe can be positioned within a portion of a patient such as for probing or moving tissue. In a further example, an elongated tube can be placed for removing fluid or material from a patient, such as to remove resected tissue from a patient.

SUMMARY

This section provides a general summary of the disclosure, and is not a comprehensive disclosure of its full scope or all of its features.

A tube can include an elongated cannulated member that has an external wall. The tube can have a selected internal diameter and external diameter based upon various selected features, such as a selected position for operation of the tube and volume and rate of removal or application of material with the tube. For example, a tube may be used for an ear, nose, and throat (ENT) procedure that may have a relatively small internal and external diameter. In addition, a tube or other instrument can be used in any appropriate selected procedure, such as a cannulated member and/or catheter for drug deliver or similar therapies in a brain, heart, vascular system. Also, suction can be formed through the instrument in any appropriate procedure. Nevertheless, a tube of any selected diameter can be used.

The tube can be formed in a selected length and shape. The user, such as a surgeon, may select to alter the shape of the tube. For example, the tube can be formed of a material that allows the user to bend the tube to a selected geometry during use. Selected materials can include aluminum or aluminum alloys that provide appropriate bending capabilities, such as bending to a selected radius without crushing or collapsing the internal diameter of the tube.

The tube may also be coated with a selected material to ensure that debris from the tube does not enter the patient. For example, an internal biocompatible coating can be positioned on the tube such that debris from the tube will not enter the patient during suction and/or irrigation of the patient with the tube. The biocompatible coating can be applied to the tube in a manner to ensure appropriate protection of the patient from debris.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a detail view of an assembled lined tube, according to various embodiments;

FIG. 2 is an exploded view of the lined tube of FIG. 1;

FIG. 6A is a partial view of the distal region of an exemplary suction instrument illustrating an exemplary tracking device arrangement, according to various embodiments;

FIG. 6B is a partial view of the distal region of an exemplary suction instrument illustrating a further exemplary tracking device arrangement, according to various embodiments.

Corresponding reference numerals indicate corresponding parts throughout the several views of the drawings.

DETAILED DESCRIPTION

Figure 3:
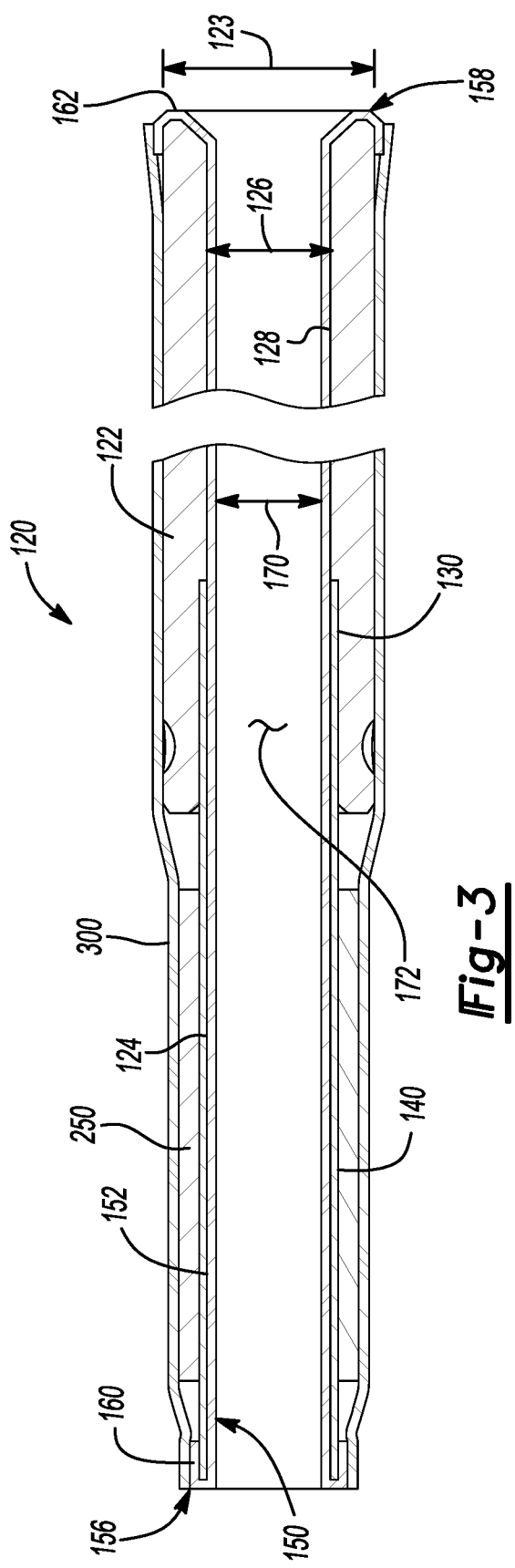
FIG. 3 is a cross-section view of a lined tube, according to various embodiments.

Example embodiments will now be described more fully with reference to the accompanying drawings.

With reference to FIG. 1, an elongated tube 20, according to various embodiments, is illustrated. The elongated tube can include an external diameter of an external tube member 21 that is defined by an external wall 22 from a selected dimension. The tube 20 can include an external structure, such as formed of a metal that has a thickness 24. The tube member 21 can, therefore, include an internal diameter defined by an inner wall 26. Positioned within the tube 20 can be a selected coating or liner 30 that has an external surface that contacts the internal wall 26 of the tube member 21. An internal surface 32 of the liner 30 then defines an internal diameter 36 of a bore 38 of the tube assembly 20. The liner 30, therefore, can include a thickness 34. The thickness of the metal 24 and the thickness of the liner 34 define the internal diameter 36 of the tube 20. The tube 20 can extend between a first end 40 and a second end 42 to define a length 44.

The external portion or tube member 21 that defines the external wall 22 can be formed of a selected material that includes selected properties. For example, the tube 20 can be selected to have a selected malleability to allow the tube 20 to be shaped while maintaining the ultimate internal diameter or at least a selected fraction thereof. Thus, the tube 20 can be bent without kinking or collapsing. Materials can be selected for the tube member 21, such as aluminum or aluminum alloys including AL 3003-O, sold by International Tube having a place of business at 1500N CR 1850E Villa Grove, IL The aluminum or aluminum alloys can be selected to achieve or allow for a selected malleability or bendability of the tube 20. The tube 20 can be formed to achieve a selected radius without crushing or closing the bore 38 or substantially reducing the internal diameter 36 of the tube 20. For example, the small suction has a bend radius of about 8 millimeters (mm) from the centerline and this can be achieved with the tube 20 formed of an aluminum as the external tube 21 while maintaining at least a selected internal diameter. The overall bend radius is a function of the outer diameter and the tube's wall thickness. In this example, the outer diameter may be, for example, about 2 mm to about 3 mm, the inner diameter may be about 1 to about 2 mm, and the wall thickness may be about 0.1 to about 1 mm. In one example, the outer diameter of the tube 21 may be about 2.3 mm, the wall thickness about 0.4 mm, and the inner diameter about 1.4 mm. In other words, the tube 20 will generally not kink or the internal cannula will not collapse.

For various applications, however, an aluminum material may be selected to have minimal contact with an environment. For example, an irrigation or suction tube used during an ear, nose and throat (ENT) procedures may be selected to have minimal contact or introduction of debris from the aluminum tube into a human patient or other animal patient. It is understood that other procedures can also be performed or that any appropriate instrument can be formed to include a coating or covering as disclosed herein. Accordingly, the internal liner 30 can be applied to the internal diameter or internal wall 26 of the aluminum tube 21 to minimize or eliminate contact or debris introduction from the aluminum tube 21 into a patient. The liner can be applied to the metal tube 21 to ensure that no debris or abrasion occurs at the internal wall 26 of the tube member 21 to ensure that debris from the tube member 21 is not introduced to the patient.

With reference to FIG. 2, the liner 30 can include an external wall 50 that can contact and adhere to the internal wall 26 of the tube member 21. The contact of the liner 30 with the tube member 21 can cause the liner 30 to adhere to the internal wall 26 of the tube member 21. The adhesion of the liner 30 to the internal wall 26 of the tube member 21 can be performed in an appropriate manner and manufacturing process. Selected manufacturing processes include application of an adhesive, extruding the liner 30 into the tube member 21, co-extruding the tube member 21 with the liner 30, or other processes. The liner 30, however, can be affixed to the internal wall 26 of the tube member 21 to substantially line and protect the tube member 21 from contact with the patient. It is also understood that the external wall 22 of the tube 21 can be covered with a selected coating, such as the material of the liner 30 or other selected materials. For example, as discussed further herein, a selected shrink-wrap (also referred to as heat shrink) material can be bonded to the external wall 22 of the tube member 21 to fix in place various structures, such as circuitry, helical wires, and/or navigation tracking devices.

According to various embodiments, the liner 30 can be fixed to the internal wall 26 of the tube member 21 by a pressure and bonding process. For example, the liner 30 can be positioned within the tube member 21, as illustrated in FIG. 1. The tube 20 can then be sealed at one end, such as the end 42, and a fluid source can be introduced into the first end 40 of the tube member 21, such as air or a selected liquid. The fluid can be pressurized within the tube member 21 to apply a force of the liner 30 into the internal wall 26 such that the external wall 50 of the liner 30 is forced against the internal wall 26 of the tube member 21. According to various embodiments, in addition to the pressure, the combination of the tube member 21 and the liner 30 can be heated to a selected temperature, such as about 105° C. (about 221° F.), but can include a heating the tube to within about 90° C. to about 120° C. (about 194° F. to about 248° F.). The pressure can be applied on the liner 30 into the tube member 21 along with the heat for a selected time, such as about 8 minutes (mins.) to about 13 mins. As an example, the pressure inside the liners may be set to about 90±10 PSI (about 620±70 kPa) for an exemplary tube having a size of 7 French, about 80±5 PSI (about 558±35 kPa) for an exemplary tube having a size of 9 French, and about 40±5 PSI (about 275±35 kPa) for the an exemplary tube having a size of 12 French.

After the selected period of time, the pressure can be removed, such as by removing the selected fluid from within the liner 30 and the heat can be removed from the combination of the liner 30 and the tube member 21. The liner 30 can, therefore, be fixed within the tube member 21 with the pressure and heat process. Generally, the liner 30 is adhered or bonded to the internal wall of the tube member 21 with enough strength to resist coming loose during bending of the tube 20 alone or in combination with suction and/or irrigation through the tube 20. In addition, a stylet or substantially stiff member may contact the liner while removing blockages without dislodging the liner. The suction and/or irrigation can be provided by commonly used suction sources for surgical procedures provided in hospitals. It is understood, however, that the tube m21 may form a portion of an instrument that may also be connected to a power console, such as the Integrated Power Console IPC® system sold by Medtronic, Inc.

In addition, the internal wall 26 of the tube member 21 can be modified, such as by abrasion or etching to increase bonding strength of the liner 30 with the internal wall 26. For example, a solution of ferric chloride (about 40% by weight and 1% by weight HCl) can be used to etch the internal wall 26. Additionally, mechanical methods can be used to etch or abrade the internal wall 26. This can increase a surface area for bonding of the external wall 50 with the etched internal wall surface 26. It is further understood, however, that the internal surface of the tube 21 may be unetched and/or polished prior to placing the liner within the tube 21.

The liner 30 can be selected material, such as polyether block amides, such as those PEBAX® materials sold by Arkema, Inc., having a place of business in France. Other appropriate materials for the liner 30 can include linear low-density polyethylene and polypropylene homopolymers, such as the PROFAX polypropylene homopolymers sold by various distributors and manufacturers. The selected material for the liner 30 can generally be selected to be flexible, wear and tear resistant, and achieve appropriate bonding with the internal wall 26 of the tube member 21.

Additionally, co-polymers or co-extruded liners 30 can also be provided or formed. For example, a coextruded liner 30 can be adhered or bonded to the internal wall 26 of the tube member 21. In a co-extruded construction an outer surface of the liner can be formed of a "sticky" material while the internal surface is formed of a smooth and/or harder material. For example, "sticky" PEBAX® 2533 may be co-extruded on the outside of "smooth" PEBAX® 6333 on the inside. Co-extrusion can be performed in any appropriate known co-extrusion process.

The liner thickness 34 of the liner 30 can be selected for various properties, but may be selected to be about 0.127 millimeters (mm) to about 0.254 mm thick. For example, a thickness of about 0.127 mm ensures that the liner 30 is at least as flexible as the tube 21 and remains in place within the tube assembly 20.

According to various embodiments, with reference to FIG. 3, a tube 120 is illustrated. The tube 120 can include two external portions, including a first external tube portion (or malleable portion) 122 and a second external tube portion (or insert) 124. The two external portions 122 and 124 can be formed of a single selected material or of different selected materials. As illustrated in FIG. 3, the first external portion 122 can include an external diameter and a central bore having an internal diameter 126 defined by an internal wall 128. The first external portion 122 can further define a second internal diameter by a second internal wall portion 130. The second wall 130 can engage or receive the second external portion 124. For example, as illustrated in FIG. 3, the second external portion 124 can include an external diameter or surface that is received and engaged in the second internal diameter defined by the wall 130 of the first external portion 122. The second external portion 124 can be fixed into the first external portion 122 according to various embodiments, such as through an adhesive, braising, welding, or other fixation mechanisms.

According to various embodiments, the first external portion 122 can be formed of a first material while the second external portion 124 is formed of a second material. It is understood, however, that the first external portion 122 and the second external portion 124 can also be formed of the same material. According to various embodiments, the first external portion 122 can be formed of an aluminum or aluminum alloy, similar to those discussed above. The second external portion 124 can be formed of a steel or steel alloy, including generally known in biocompatible stainless steel alloys. The first external portion 122 can therefore include various malleable features, including those discussed above. The second external portion 124 can be more rigid or stiff for various purposes, including those discussed herein.

The tube 120, however, can include a substantially continuous internal diameter through the first external portion 122 and the second external portion 124 or an appropriate variable internal diameter. Nevertheless, the second external portion 124 can include or have an internal wall 140 that defines the internal diameter 126. Positioned within the internal diameter and on the first wall 128 of the first external portion 122 and the second wall 140 of the second external portion 124 can be a liner 150.

The liner 150 can be substantially similar to the liner 30 discussed above and include an external wall or surface 152 to engage the internal wall 140 of the second external portion 124 and the internal wall 128 of the first external portion 122. Additionally, the liner 150 can be affixed or adhered to the tube 120 similar to the method as discussed above for fixing the liner 30 within the tube member 21. The liner 150 can have a selected thickness, as discussed above. The liner, therefore, can define an internal diameter 170 of a bore 172 of the tube assembly 120.

According to various embodiments, the liner 150 can extend from the ends or open ends of the tube 120, such as the first end 156 and the second end 158, to engage a wraparound an exterior surface of the tube 120. For example, the liner can extend around into an exterior of the tube 120 at the first end 156 a first liner extension portion 160 and around the second end 158 of the tube 120 at a second liner extension portion 162. The liner extension portions 160 and 162 can be adhered to the tube 120 in a similar manner as discussed above. Additionally, it is understood that a tube, such as the tube 20 illustrated above in FIGS. 1 and 2, can also include portions of the liner 30 that extend exterior to the internal surface 26 of the tube member 21, such as over an exterior surface 22 thereof. Accordingly, the liner can extend onto an external surface of a tube whether the tube is formed as a single one-piece member or formed of multiple portions, as illustrated in FIG. 3.

In addition, an entire exterior of the tube, including the tube 20 and the tube 120, can be covered with the respective liners 30, 150. According to various embodiments, however, an external surface of the respective tubes, can be covered by other materials. For example, a heat shrink wrap 300 (FIG. 3), can be used to cover the tube 21. The heat shrink wrap can include heat shrink wrap such as that disclosed in U.S. patent application Ser. No. 13/751,032 filed on Jan. 25, 2013, incorporated herein by reference.

Referring now to FIGS. 4-7, and continuing reference to FIGS. 1-3, the lined tube, according to various embodiments, can be included or used as a navigated malleable surgical instrument 200, as will be described in greater detail herein. In one exemplary embodiment, the malleable surgical instrument 200 can be used for suction, including fluid and tissue removal during ENT procedures. Again, it is understood that the suction tube can be used for any appropriate procedure or that other appropriate instruments can be covered as discussed herein. It will be appreciated, however, that the navigated malleable surgical instrument 200 can be used in various other surgical procedures as may be desired and can be provided in the form of a malleable or flexible endoscope, a malleable or flexible catheter, and/or a malleable or flexible cannulated member. Thus, while the following description continues with reference to a navigated malleable suction instrument 200, the discussion is also applicable to the various surgical instruments, as discussed above.

Figure 4:
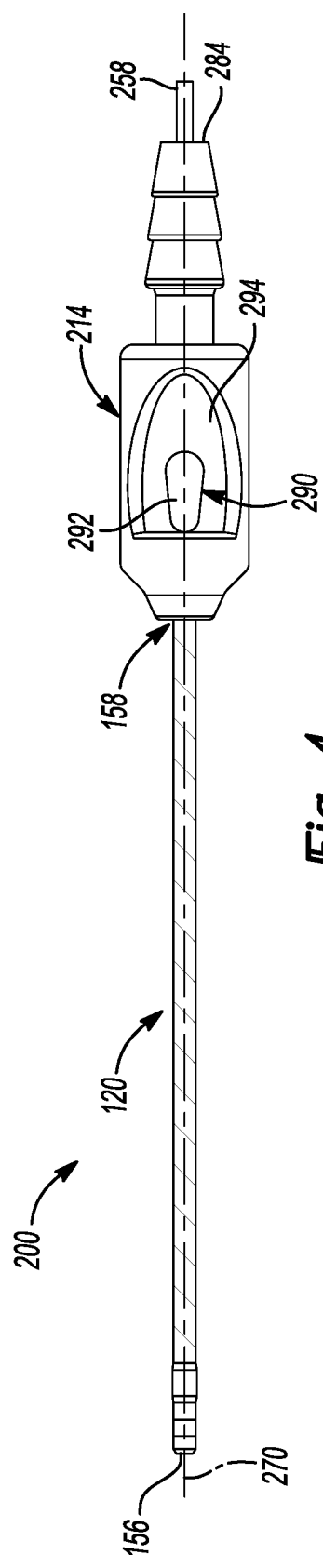
FIG. 4 is a top plan view of an exemplary malleable suction instrument, according to various embodiments.
Figure 5:
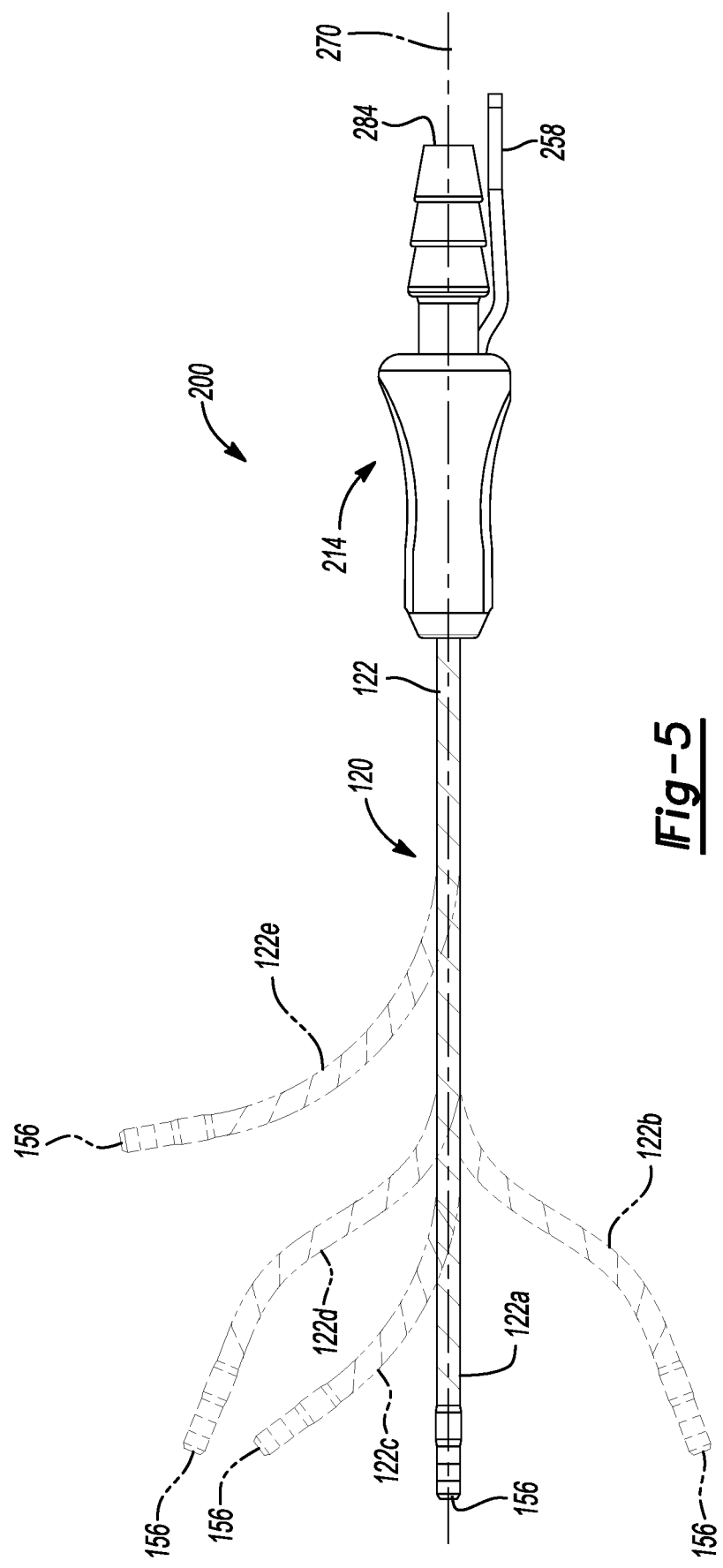
FIG. 5 is a view of exemplary bent or formed configurations of the exemplary malleable suction instrument, according to various embodiments.
Figure 7:
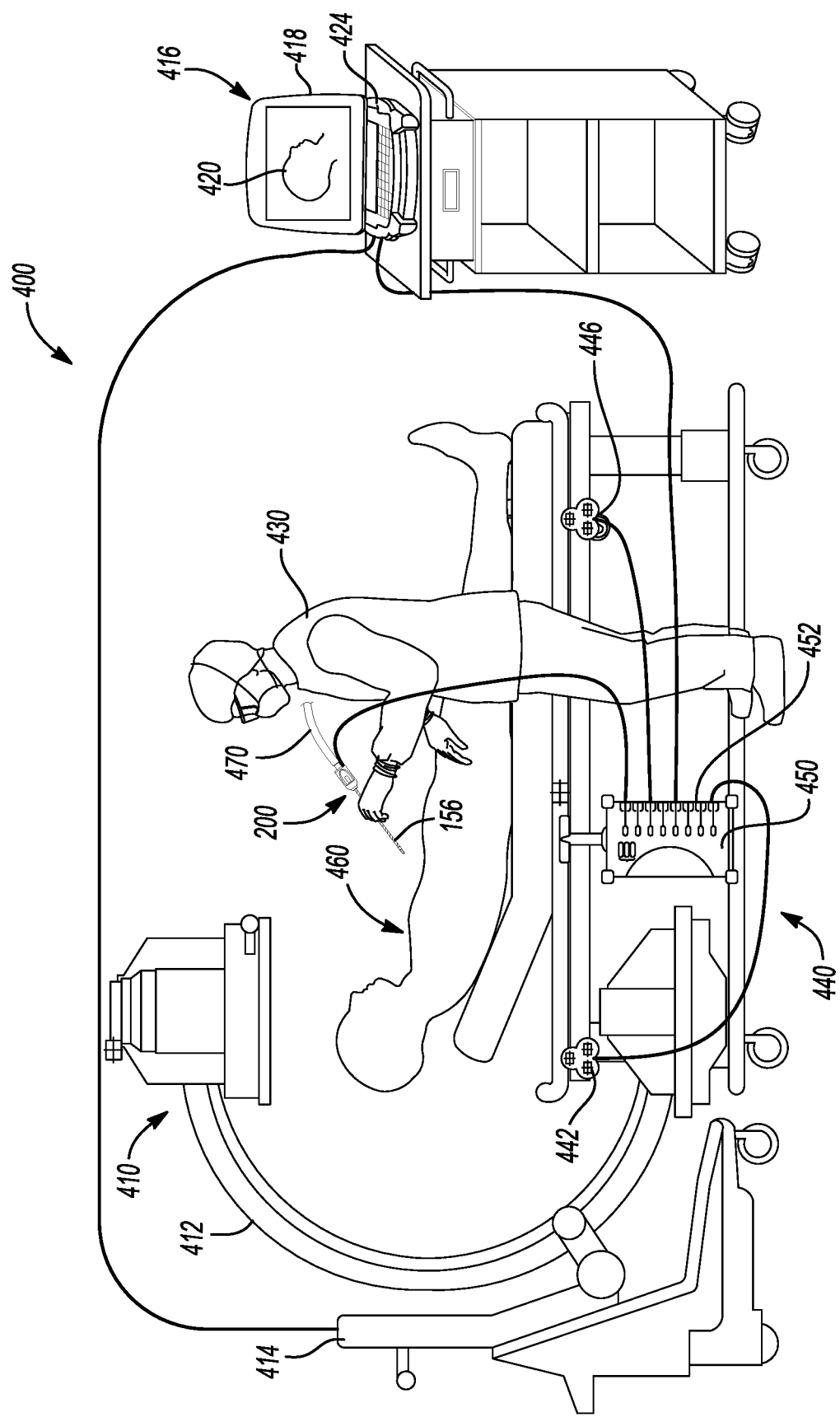
FIG. 7 is an environmental view of an exemplary navigation system according to the principles of the present disclosure, according to various embodiments.

Accordingly to various embodiments, as illustrated in FIG. 4, a tube, such as the tube 120 can be used with the navigated malleable suction instrument 200 (also referred to as instrument 200 herein) that includes a handle or graspable portion 214 for manipulation by a user, as illustrated in FIG. 7. It is further understood that the tube 20 can also be used with the handle portion 214 and the following discussion of the tube 120 is merely exemplary. A connector 284, such as a suction or irrigation source connection, can extend from the handle 214. Also a cable connector 258 can extend from the handle 214. The cable connector 258 can allow for connection of one or more tracking devices 250 (FIG. 6A) and/or tracking devices 250' (FIG. 6B) to various systems, such as the tracking system discussed herein. The tube 120 can be malleable and/or shapeable as illustrated in FIG. 5. Also, according to various embodiments, the tube 120 can also include various tracking devices, including the tracking devices 250, 250' as illustrated in FIGS. 6A and/or 6B. Accordingly, a user, as illustrated in FIG. 7, can bend the tube 120 to various configurations for use in a procedure, including that as disclosed in U.S. patent application Ser. No. 13/751,032 filed on Jan. 25, 2013, incorporated herein by reference. A brief description of the use of the lined tube, according to various embodiments, including the tube 120, will be discussed herein.

The instrument 200 can be configured for a single use such that it would be disposed after such use. The tube assembly 120 can include a malleable elongated tubular body, which can include the outer portion 122. The tubular body 122 can include an outer diameter 123 and the inner diameter 126. The end 162 may be coupled to the handle assembly 214 and the second opposite end 160 extends away from the handle 214. The second end of the first outer portion 122 may receive the second outer portion 124 (also referred to as an insert) and/or be coupled to the tracking device 250, as discussed herein. The malleable elongated body 122 can be formed from various aluminum alloys, such as AL 3003-O, sold by International Tube having a place of business at 1500N CR 1850E Villa Grove, IL, such that it is malleable to facilitate being bent or formed into various configurations and retaining the bent or formed configuration, as will be discussed herein. The body 126 can also be provided in various lengths and diameters, including 7, 9 and 12 French diameters.

The insert portion 124 can be configured to provide non-malleable support for at least the tracking device 250. Insert portion 124 can include an outer diameter defined by the wall 140 that is substantially equal to the inner diameter defined by the inner wall 130 and an inner diameter that is substantially equal to the inner diameter 126 of malleable elongated body 122, as also shown in FIG. 3. In this manner, the substantially equal inner diameter 126 of both the first portion 122 and the second portion 124 can provide for a substantially constant flow path 220 for suction. It should be appreciated, however, that the inner diameter can also be provided with varying dimensions.

The handle assembly 214 can include a suction adjustment feature 290 which can be in the form of a bore 292 extending from an outer surface 294 of the handle assembly 214 and into fluid communication with the suction passage 220 through the tube 120. In operation, a surgeon or user 50 of the instrument 200 can place their thumb or another object over the bore 292 to vary an opening of the bore 292 and thus vary an amount of suction pressure realized in the flow path or passage 220. For example, if the bore 292 is left completely open or uncovered, a majority if not all of the suction will be through the bore 292 and not the first end 156 of insert portion 130. On the other hand, if the bore 292 is completely covered or closed off, a maximum amount of suction will be realized at end 172. Varying the opening of bore 292 between fully closed and fully opened can therefore correspondingly vary an amount of realized suction at end 156.

In operation and with additional reference to FIG. 5, the malleable elongated body 122 can be bent into various configurations, as generally shown by the exemplary configurations 122a-d. The malleable nature of body 122 can provide the ability for body 122 to be bent into such various configurations without kinking and can maintain the various configurations until bent or shaped into another configuration. In an initial or selected configuration 122a, the tube 120 can extend along a substantially straight axis 270. The malleable tube 122 can be bent to the non-straight configurations 122b-d or other selected configurations. Further, malleable body 122 can be bent or shaped as discussed above without requiring additional tools, such as a mandrel to facilitate the bending. This is advantageous, for example, in that a surgeon can bend body 122 multiple times by hand during a procedure in close proximity to the patient without having to resort to additional tools or other equipment to facilitate the bending while performing the procedure.

The tube assembly 120 can include a polymeric outer heat shrink 300 covering the entire assembly, as shown in detail in FIG. 6A. Thus, the heat shrink 300 can cover the elongated body 122, the insert portion 124, and the tracking device 250 including any wires or connectors extending along the tube assembly 120, such as wires that may be helically wound along the body 122 as disclosed in U.S. patent application Ser. No. 13/751,032 filed on Jan. 25, 2013, incorporated herein by reference. The heat shrink 300 can provide an outer covering or shell over the tube assembly 120 and sensor arrangement 250 while providing sufficient flexibility for both bending of the body 122 and slight relative movement of any helically wound wires as a result of the bending. In this regard, the wires can be moveably captured between the heat shrink and the tubular body. The heat shrink covering can also serve as an electric isolation and/or physical barrier. Thus, the liner 150 need not extend over the outside of the tube 120. It is understood, however, that the liner 150 may extend over the outside of the tube 120.

With further reference to FIG. 6A, the tracking device 250 is shown associated with instrument 200. The tracking device 250 can include a plurality of oval coil assemblies positioned around the sleeve 124 near the distal tip 156. In one exemplary configuration, two to four coil assemblies can be positioned about sleeve 124 proximate distal tip 222. In the exemplary configuration illustrated, coil assemblies 250a-c can be circumferentially spaced around sleeve 124 near the distal tip 156, further an axial coil 304 can be positioned proximally of the coil assemblies 250a-c, as shown in FIG. 6A. The axial coil can be wound around the axis 270 of the tube assembly. Thus, as is understood in the art, at least six degrees of freedom of tracking information can be determined regarding the distal end 156 of the tube 120. The coil assemblies 250a-c can be formed in various selected shapes, such as elliptical, circular, or oval. A further discussion of coil assemblies 250a-c and axial coil 304 can be found in U.S. application Ser. No. 13/016,740, filed on Jan. 28, 2011 and entitled "Method and Apparatus for Image-Based Navigation", incorporated herein by reference.

With reference to FIG. 6B a further exemplary tracking device 250' is illustrated. It is understood that the tracking device 250' can be used separately or in conjunction with the tracking device 250. The tracking device 250' is described in detail in U.S. patent application Ser. No. 13/751,032 filed on Jan. 25, 2013, incorporated herein by reference, and will be described briefly here. Generally, the tracking device 250' can include tracking device members 250'a-c that are associated with an instrument 200', similar to the instrument 200 discussed above. The instrument 200' and/or a tube 120' can be substantially similar and/or identical to the instrument 200 and tube 120 discussed above. The tracking device 250' may be provided in a different configuration. For example, the tube 120' can include an insert portion 124' that can be configured to provide non-malleable support for at least the tracking device 250' and a selected internal and external diameter as discussed above. The insert can include a selected number of grooves 310a, 310b to receive the tracking devices 250'a-c. The grooves 310a, 310b can be formed in flattened sides 312a, 312b of the insert 124'. Connections 314 can be provided between the tracking devices 250' and the navigation system 400 as discussed above and herein. The tube 120' can include a liner 30' similar and/or identical to the liner 30 discussed above along with the heat shrink 300. Thus, the tracking device assembly 250' may also be used, alternatively and/or in combination with the tracking device 250.

FIG. 7 is a diagram schematically illustrating an environmental view of an image-guided navigation system 400 for use in the non-line-of-site navigating of a surgical instrument 200, such as a navigable malleable suction device or suction instrument, according to various exemplary embodiments of the present disclosure. Exemplary navigation systems include those disclosed in U.S. Pat. No. 7,366,562, issued on Apr. 29, 2008 to John H. Dukesherer et al. and U.S. Pat. App. Pub No. 2008/0132909, published Jun. 5, 2008, to Bradley A. Jascob et al., both incorporated herein by reference. Commercial navigation systems include the StealthStation® AxiEM™ Surgical Navigation System sold by Medtronic Navigation, Inc. having a place of business in Louisville, Colorado, USA. It should be appreciated that while the navigation system 400 and suction instrument 200 are generally described in connection with an ear, nose and throat (ENT) procedure, navigation system 400 and suction instrument 200 can be used in various other appropriate procedures.

Generally, the navigation system 400 can be used to track a location of an exemplary suction instrument 200, including the distal tip 156 thereof. The instrument 200 can include an exemplary flexible printed circuit sheet (not illustrated). Navigation system 400 can generally include an optional imaging system 410, such as a fluoroscopic X-ray imaging device configured as a C-arm 412 and an image device controller 414. The C-arm imaging system 410 can be any appropriate imaging system, such as a digital or CCD camera, which are well understood in the art. Image data obtained can be stored in the C-arm controller 414 and sent to a navigation computer and/or processor controller or work station 416 having a display device 418 to display image data 40 and a user interface 420. It is understood that any appropriate image data (e.g. magnetic resonance image data, computed tomography image data, SPECT image data, etc.) can be acquired of the subject pre-operatively and/or intra-operatively for use with the navigation system 400.

The work station 416 can also include or be connected to an image processor, navigation processor, and a memory to hold instruction and data. The work station 416 can include an optimization processor that assists in a navigated procedure. It will also be understood that the image data is not necessarily first retained in the controller 414, but may also be directly transmitted to the workstation 416. Moreover, processing for the navigation system and optimization can all be done with a single or multiple processors all of which may or may not be included in the work station 416.

The work station 416 provides facilities for displaying the image data 420 as an image on the display device 418, saving, digitally manipulating, or printing a hard copy image of the received image data. A user interface 424, which may be a keyboard, mouse, touch pen, touch screen or other suitable device, allows a physician or user 430 to provide inputs to control the imaging device 410, via the C-arm controller 414, adjust the display settings of the display device 418, and/or otherwise control the navigation system 400.

The navigation system 400 can further include a tracking system, such as an electromagnetic (EM) tracking system 440. The discussion of the EM tracking system 440 can be understood to relate to any appropriate tracking system. The EM tracking system 440 can include a localizer, such as a coil array 442 and/or second coil array 444, a coil array controller 450, a navigation probe interface 452, and the trackable suction instrument 200. Instrument 200 can include the instrument tracking device or devices 250. The tracking device 250 can include an electromagnetic coil to sense a field produced by the localizing coil arrays 442, 446 and provide information to the navigation system 400 to determine a location of the tracking device 250. The navigation system 400 can then determine a position of the distal tip 156 of the suction instrument 200 to allow for navigation relative to a patient 460 and patient space.

The EM tracking system 440 can use the coil arrays 442, 446 to create an electromagnetic field used for navigation. The coil arrays 442, 446 can include a plurality of coils that are each operable to generate distinct electromagnetic fields into the navigation region of the patient 460, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The localizers 442, 446 can be controlled or driven by the coil array controller 450. The coil array controller 450 can drive each coil in the localizers 442, 446 in a time division multiplex or a frequency division multiplex manner. In this regard, each coil may be driven separately at a distinct time or all of the coils may be driven simultaneously with each being driven by a different frequency.

Upon driving the coils in the localizers 442, 446 with the coil array controller 450 electromagnetic fields are generated within the patient 460 in the area where the medical procedure is being performed, which is again sometimes referred to as patient space. The electromagnetic fields generated in the patient space induce currents in the tracking device 250 positioned on or in the suction instrument 200. These induced signals from the tracking device 250 can be delivered to the navigation probe interface 452 and subsequently forwarded to the processor 416. The navigation probe interface 452 can also include amplifiers, filters and buffers to directly interface with the tracking device 250 in the instrument 200. Alternatively, the tracking device 250, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 450.

The tracking system 440, if it is using an electromagnetic tracking assembly, essentially works by positioning the localizers 442, 446 adjacent to the patient 460 to generate an electromagnetic field, which can be low energy, and generally referred to as a navigation field. Because every point in the navigation field or patient space is associated with a unique field strength and directions, the electromagnetic tracking system 440 can determine the position of the instrument 200 by measuring the field strength and directions or components thereof at the tracking device 250 location. The coil array controller 450 can receive the induced signals from the tracking device 250 and transmit information regarding a location, where location information can include degree of freedom information, including x, y, and z position and roll, pitch, and yaw orientation information, of the tracking device 250 associated with the tracked suction instrument 200. Accordingly, six degree of freedom (6 DOF) information can be determined with the navigation system 400.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of performing a procedure;
providing a tube member in a first configuration and extending from a proximal end to a distal end having at least a first tube member formed from a bendable and malleable aluminum or aluminum alloy tube, the tube member having an internal wall extending from the proximal end to the distal end that is lined with a liner having an external wall that contacts and is fixed along and throughout an entire internal surface of the internal wall;

bending the provided tube member by hand to a desired shape from the first configuration to a second configuration to retain the second configuration without collapsing or closing an open bore extending through the tube member from the proximal end to the distal end while maintaining the liner within the tube member throughout the use of the tube member; and after bending the provided tube member by hand from the first configuration to the second configuration moving the bent provided tube member in the second configuration having the open bore relative to a subject while retaining the second configuration and inhibiting debris from the aluminum or aluminum alloy tube from exiting and passing through the tube member.

2. The method of claim 1, further comprising:
operating a tracking system to track a location of a distal tip of the bent provided tube member.

3. The method of claim 2, further comprising:
operating a navigation system to illustrate the tracked location of the bent tube member relative to the subject with a display device.

4. The method of claim 3, further comprising:
providing the tube member with an external cover to cover at least a tracking member fixed to the tube member.

5. The method of claim 4, further comprising:
prohibiting the debris from the tube member from entering the subject due at least to the liner being formed from a tear and wear resistant material.

6. The method of claim 1, further comprising:
retaining the tube member in the second configuration after bending the tube member while moved relative to the subject.

7. The method of claim 1, further comprising:
providing a suction through the open bore of the tube member to remove debris from the subject while inhibiting aluminum debris from the aluminum or aluminum alloy tube from passing through the tube member.

8. The method of claim 1, further comprising:
providing irrigation through the open bore of the tube member to irrigate a portion of the subject while inhibiting aluminum debris from the aluminum or aluminum alloy tube from passing through the tube member.

9. The method of claim 7, further comprising:
holding the tube member with a handle and adjusting the suction through the tube member through the handle.

10. The method of claim 1, further comprising:
disposing of the tube member after use.

11. The method of claim 1, wherein bending the provided tube member includes bending the tube member by hand and without tools before performing the procedure.

12. The method of claim 1, wherein the liner is wear and tear resistant and the method further includes inhibiting debris from the tube member from exiting and passing through the tube member when in use with the liner during suction or irrigation using the tube member.

13. The method of claim 1, wherein bending the provided tube member includes bending the proximal end of the tube member that is formed of a malleable material by hand while a distal stiffer end of the tube member does not bend.

14. The method of claim 1, wherein providing the tube member further includes providing a tube member having a first proximal malleable aluminum or aluminum alloy tube and a second distal tube, wherein a second distal tube is stiffer than the first proximal malleable aluminum or aluminum alloy tube.

15. The method of claim 14, wherein bending the provided tube member includes bending the first proximal malleable aluminum or aluminum alloy tube into the second configuration without kinking or collapsing the internal wall of the first proximal malleable aluminum or aluminum alloy tube.

16. The method of claim 15, further comprising:
providing a tracking device on the second distal tube used to track a location of the tube member.

17. The method of claim 1, wherein providing a tube member that is lined with a liner further includes providing a liner having a first liner extension portion extending around a first end of the tube member and a second liner extension portion extending around a second end of the tube member, wherein the liner remains fixed to the tube member throughout the use of the tube member.

18. The method of claim 17, further comprising providing an external member extending over the tube member and the first and second liner extension portions.

19. The method of claim 16, further comprising operating a navigation system to track the tracking device and illustrate a tracked location of the tube member relative to the subject with a display device.

* * * * *

UNITED STATES PATENT AND TRADEMARK OFFICE
CERTIFICATE OF CORRECTION

PATENT NO. : 11,883,063 B2
APPLICATION NO. : 16/404063
DATED : January 30, 2024
INVENTOR(S) : Andrew Wald et al.

Page 1 of 1

It is certified that error appears in the above-identified patent and that said Letters Patent is hereby corrected as shown below:

On the Title Page

Page 4, Column 1, item (56) Other Publications, Line 40, Delete "claimss" and insert --claims-- therefor In the Specification Column 2, Detailed Description, Line 62, After "IL", insert --.--

Column 4, Detailed Description, Line 23, Delete "m21" and insert --member 21-- therefor Column 7, Detailed Description, Line 3, Delete "126" and insert --122-- therefor Column 10, Detailed Description, Line 28, Delete "450." and insert --452.-- therefor Signed and Sealed this
Fifth Day of March, 2024

Katherine Kelly Vidal
*Director of the United States Patent and Trademark Office*